Figure 4:
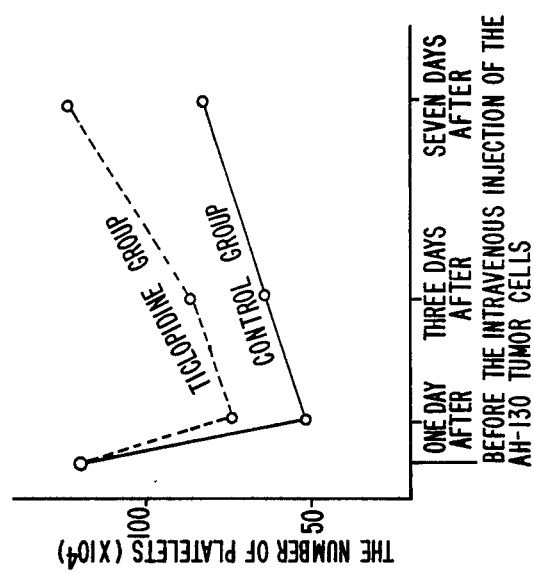

United States Patent [19]

Suzuki

[11] Patent Number: 4,963,559

[45] Date of Patent: Oct. 16, 1990

[54] METHOD OF TREATING CANCER AND CANCER METASTASIS

[75] Inventor: Tadao Suzuki, Tokyo, Japan

[73] Assignee: Sanofi, Paris, France

[21] Appl. No.: 436,969

[22] Filed: Oct. 27, 1982

Related U.S. Application Data

[63] Continuation of Ser. No. 972,819, Dec. 26, 1978, abandoned.

[30] Foreign Application Priority Data

Jan. 6, 1978 [JP] Japan ................................. 53-465

[51] Int. Cl.$^5$ ............................................. A61K 31/44
[52] U.S. Cl. ................................................... 514/301
[58] Field of Search .................. 424/263, 250; 514/301

[56] References Cited

U.S. PATENT DOCUMENTS 4,051,141  9/1977  Castaigne ............................ 424/256

Primary Examiner—Jerome Goldberg
Attorney, Agent, or Firm—Wegner & Bretschneider

[57] ABSTRACT

The present invention relates to an agent for treating cancer and preventing cancer metastasis consisting of a compound selected from 5-(2-chlorobenzyl)-4,5,6,7-tetrahydro-thieneo[3,2-c]pyridine and its therapeutically acceptable acid addition salts.

The therapeutically acceptable acid addition salt is in particular the hydrochloride named Ticlopidine.

19 Claims, 2 Drawing Sheets

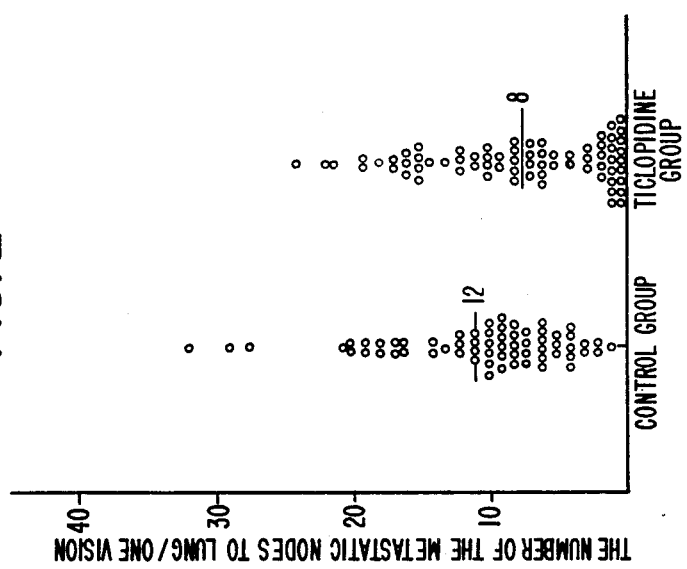
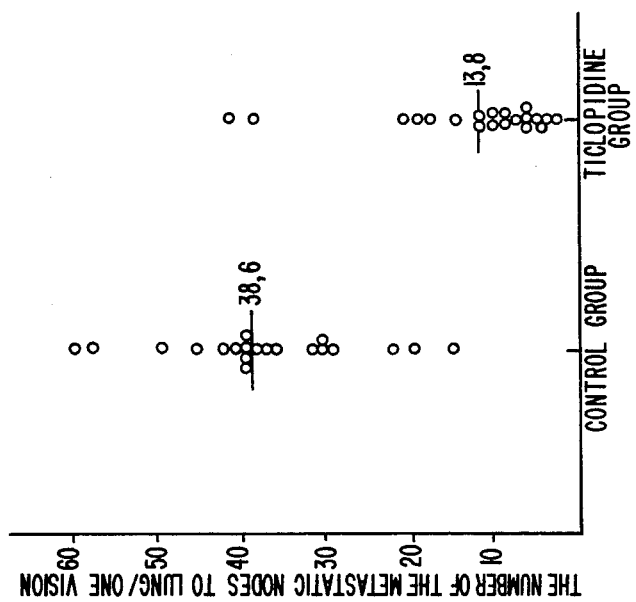

METHOD OF TREATING CANCER AND CANCER METASTASIS

This is a continuation, of application Ser. No. 972,819, filed Dec. 26, 1978 now abandoned.

DESCRIPTION

The present invention relates to a method of treating cancer and cancer metastasis using 5-(2-chlorobenzyl)-4,5,6,7-tetrahydrothieno[3,2-c]pyridine or a salt thereof as active ingredient.

5-(2-chlorobenzyl)-4,5,6,7-tetrahydrothieno[3,2-c]pyridine is a compound represented by the formula:

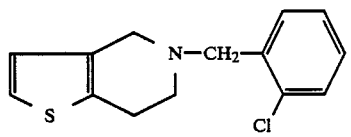

(I)

The common name of the hydrochloride thereof is Ticlopidine.

Ticlopidine and its process of preparation have been disclosed in U.S. Pat. No. 4,051,141.

The present invention will be described with reference to Ticlopidine, but the other therapeutically acceptable acid addition salts or the free base would also achieve substantially same effects.

For the treatment of cancer, three kinds of treatments, that is chemotherapy, surgical treatment and radiotherapy, are mainly used. However, satisfactorily therapeutic effects have not been achieved as concerns the prevention from relapse and prolongation of life. One of the reasons for the unsatisfactory results is that, even if primary lesion can be reduced or castrated by these treatments, cancer develops (metastasizes) and proliferates at major organs of different regions from the primary lesion, such as brain, lung, liver, etc. and fatal results would be caused. Accordingly, it is of extreme importance for the complete cure of cancer that the development (metastasis) of cancer at different regions be prevented in addition to these treatments for reduction or surgical castration of primary cancer lesion.

The inventor has found that Ticlopidine is useful for the solution of the aforementioned problems. According to the present invention, when Ticlopidine is previously administered in rats which had been intravenously injected with AH-130 tumor cells through the caudal vein, generation of metastatic nodes at lung is markedly prevented.

The present invention will be explained hereinafter with reference to the results of animal experiments using rats as shown in FIGS. 1 and 2 of the accompanying drawings.

FIG. 1 shows the prevention effect from tumor metastasis in case of intravenous injection of Ticlopidine. In this experiment five Donryu-strain rats, each for control group and for Ticlopidine group, were used. After diluting with biological saline solution to a certain number of AH-130 tumor cells, $2 \times 10^6$ tumor cells per one rat were injected through the caudal vein. The rats were sacrificed five days after and the lungs were isolated. Each of the lung sections was stained in accordance with the hematoxylin-eosin staining method and the number of the metastatic nodes in lungs was counted at every five visual fields per one rat. When counted by this method, a mean number of the metastatic nodes in lungs at each visual field was 38.6 in the control group, while a mean number of the lung-metastatic nodes at each visual field was 13.8 in the Ticlopidine group which had been previously intravenously administered 2 hours before the intravenous injection of the tumor cells at the dose of 5 mg of Ticlopidine/kg. It is clear that the number of the metastatic nodes in the Ticlopidine group is far less than that of the control group.

FIG. 2 shows the prevention effect from tumor metastasis when Ticlopidine was orally administered. $2 \times 10^6$ AH-130 tumor cells per one rat were injected through caudal vein to the Ticlopidine group consisting of five rats which had been orally administered through a peroral sonde at the dose of 20 mg of Ticlopidine/kg twice, 24 hours before and 2 hours before the intravenous injection of the tumor cells.

The number of nodes metastasized in lungs was counted 5 days after the tumor cell injection. The number of the lung-metastatic nodes was counted at each of thirteen of fourteen visual fields per one rat using a microscope with a magnefication of 100. The mean number of the metastatic nodes per one visual field was 12 in the control group which was not pretreated with the drug, while in the Ticlopidine group the mean number of the metastatic nodes per one visual field was 8. The number of the metastatic nodes was therefore significantly smaller in the Ticlopidine group than in the control group.

Summarizing the results of the experiments above, it is understood that both intravenous and oral administration of Ticlopidine to rats prevent the tumor cells from metastasis thereof to the lungs.

Figure 3:
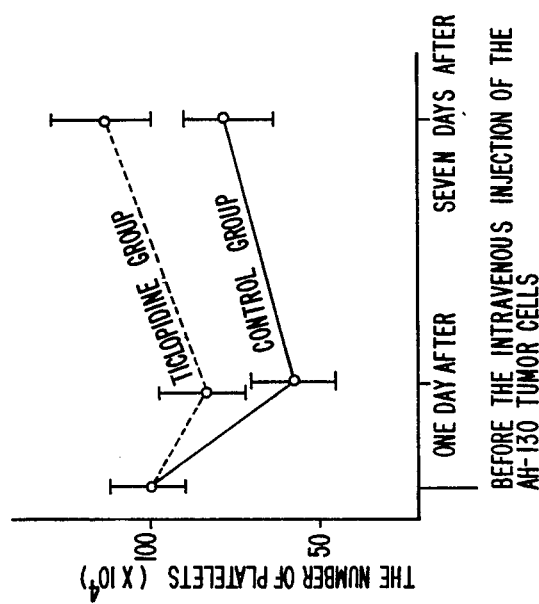

Studying this from a viewpoint of activity mechanism, the latter is as follows. The injection of the AH-130 tumor cells into caudal veins of rats induces a transient decrease of platelet counts. FIGS. 3 and 4 of the accompanying drawings show comparisons in the platelet count variations between the control group and the Ticlopidine group after the intravenous injection of the AH-130 tumor cells; FIG. 3 indicates the case in which Ticlopidine was previously administered intravenously to rats at the dose of 5 mg/kg 2 hours before the intravenous injection of the tumor cells, and FIG. 4 indicates the platelet count variation in the case in which Ticlopidine was previously administered twice orally to rats 24 hours before and 2 hours before at the dose of 20 mg/kg each.

From the results shown in FIGS. 3 and 4, it can be seen that Ticlopidine obviously restrains a transient reduction of platelet counts induced by intravenous injection of the tumor cells both in intravenous administration and in oral administration. As one of the influences which the tumor cells exert one living body, platelet coagulation activity as stated above is observed. It is believed that, by this activity due to the tumor cells, thrombus or embolism occurs in blood tubelets or other organs, and the tumor cells attach thereto and proliferate so that cancer is developed (or metastasized).

It is therefore assumed that the effect of Ticlopidine preventing the platelet from coagulation would prophylactically eliminate an initial stage of cancer metastasis. However, in similar experiments using Dipyridamol, which is well known as having inhibition activity on platelet coagulation, the platelet coagulation activity induced by the tumor cells could be prevented but development (or metastasis) of cancer could not be prevented.

Reconsidering the present invention from this fact, it is thought that the prevention effect of Ticlopindine from metastasis or development of cancer might not be based merely on the prevention of platelet from coagulation, but on a direct attack against the tumor cells, that is, Ticlopidine might have an anticancer property in itself.

As stated above, the action mechanism of the present invention is not clearly understood. It is clear, however, that Ticlopidine can inhibit development (or metastasis) of cancer.

A further advantage achieved by the present invention is that Ticlopidine is a pharmaceutical agent having an extremely high safety.

In general, pharmaceutical agents which are conventionally employed as hemotherapeutic agents against cancer have serious side effects or toxicity, and physical and mental debilities of patients are encountered even if proliferation of cancer is prevented; thus these agents cannot be administered to patients with clinical safety. On the other hand, acute toxicity of Ticlopidine in oral administration, which was measured as a $LD_{50}$ dose in animals, is low, e.g., 1780 mg/kg in male rats, 1800 mg/kg in female rats, 850 mg/kg in male mice and 600 mg/kg in female mice, respectively.

In addition, the toxicity in the case of daily oral administration of ticlopidine to animals for a long period of time is also low. Even if Ticlopidine is daily administered orally to rats at the dose of 40 mg/kg for 1 month, at the dose of 30 mg/kg for 6 months and at the dose of 30 mg/kg for 1 year and 6 months, and to monkeys at the dose of 75 mg/kg for 1 year, no abnormalities in general symptoms of these animals, clinical test data as well as pathological findings in major organs are observed. Further, even when Ticlopidine is orally administered daily to pregnant rabbits at the dose of 200 mg/kg for 12 consecutive days during organ formation, no fatal malformation is developed.

As stated above, extremely high safety of Ticlopidine is noted in animal experiments. Furthermore, notwithstanding platelet coagulation activity is potentially inhibited by its internal use to human daily at the daily dose of 100 to 500 mg for 2 to 3 months, no serious side effect not any abnormalities are observed either in general clinical test data. Therefore, Ticlopidine is expected to be an ideal anticancer and/or cancer metastasis preventing agent having high safety.

For example, a dose of 100 to 200 mg per day would be suitable for clinical use as an anticancer and/or cancer metastasis preventing agent, the active ingredient being combined with the usual pharmaceutically acceptable carriers or vehicles in dosage forms for oral or parenteral administration such as capsules, tablets or injectable solutions.

Having now described my invention what I claim as new and desire to secure by Letters Patent Is:

1. A method for the prevention or treatment of pulmonary tumor metastasis in a mammal which comprises administering to a mammal 5-(2-chlorobenzyl)-4,5,6,7-tetrahydrothieno pyridine or its therapeutically acceptable acid addition salts, which compound being administered in an effective amount thereof.

2. The method of claim 1 wherein the metastasis is decreased.

3. The method of claim 2 wherein the metastasis is prevented.

4. The method of claim 1 which comprises further, inhibiting the spread of tumors to the lungs of said mammals.

5. The method of claim 1 wherein the administration is oral.

6. The method of claim 1 wherein the administration is intravenous.

7. The method of claim 1 which comprises decreasing the metastasis without only causing blood platelet coagulation inhibition.

8. The method of claim 1 wherein the compound is the hydrochloride salt.

9. The method of claim 1 wherein the compound is administered to the mammal in a daily dosage of 100 to 500 mg.

10. The method of claim 9 wherein the administration is carried out for two to three months.

11. The method of claim 9 wherein the compound is administered to the mammal in a daily dosage of 100 to 200 mg.

12. The process of claim 11 wherein the administration is oral.

13. The process of claim 11 wherein the compound is the hydrochloride salt.

14. A method of the prevention or treatment of tumor metastasis in a mammal which comprises administering to a mammal 5-(2-chlorobenzyl)-4,5,6,7-tetrahydrothieno pyridine or its therapeutically acceptable acid addition salts, and preventing the generation of metastatic tumor nodes in the lungs of said mammal, the compound being administered in an effective amount thereof.

15. A method for the treatment of pulmonary tumor metastasis in a mammal which comprises administering to a mammal in need thereof, an effective amount of a pharmaceutical composition comprising a compound selected from the group consisting of 5-(2-chorobenzyl)-4,5,6,7-tetrahydrothieno pyridine and its therapeutically acceptable acid addition salts, and a pharmaceutically acceptable carrier, and decreasing metastasis of tumor nodes in said mammel.

16. A method for the prevention or treatment of pulmonary metastasis in a mammal which comprises administering to said mammal an effective amount of 5-(2-chlorobenzyl)-4,5,6,7-tetrahydrothieno pyridine or its therapeutically acceptable acid addition salts and a suitable pharmaceutical carrier.

17. The method of claim 16 wherein the compound is the hydrochloride salt.

18. The method of claim 16 wherein the compound is administered to the mammal in a daily dosage of 100 to 500 mg.

19. A method for the prevention or treatment of pulmonary tumor metastasis in a mammal which comprises administering to said mammal in need thereof an effective amount of a pharmaceutical composition comprising a compound selected from the group consisting of 5(2-chlorobenzyl)-4,5,6,7-tetrahydrothieno pyridine and its therapeutically acceptable acid addition salts, which composition is effective in the treatment of AH-130 tumor cells.

* * * * *